United States Patent [19]

Muldashev et al.

[11] 4,384,374

[45] May 24, 1983

[54] HOMOTRANSPLANT FOR LAYER-BY-LAYER KERATOPLASTY

[76] Inventors: Ernst R. Muldashev, ulitsa Rossiiskaya 17/2, kv. 94; Rafik T. Nigmatullin, ulitsa Vostretsova 14, kv. 19, both of Ufa, U.S.S.R.

[21] Appl. No.: 248,052

[22] Filed: Mar. 27, 1981

[51] Int. Cl.$^3$ ............................ A61F 1/16; A61F 1/24
[52] U.S. Cl. ................................................. 3/13; 3/1; 8/94.11; 128/1 R
[58] Field of Search ............. 3/13, 1; 128/1 R, 334 R, 128/305; 8/94.11

[56] References Cited

U.S. PATENT DOCUMENTS 3,563,228  2/1971  Seiderman ............................. 3/1 X
4,120,649  10/1978 Schechter ............................ 8/94.11
4,239,492  12/1980 Holman et al. ...................... 8/94.11

OTHER PUBLICATIONS

J. C. Tanner, Jr. et al., Lamellar Keratoplasty, Eye, Ear, Nose and Throat Monthly, vol. 47, No. 8, Aug. 1968, pp. 27-31.

M. W. Dunn et al., F. Collagen-Derived Membrane, 1967, Science, vol. 157, No. 3794, pp. 1329-1330.

N. A. Puchkovskaya, Transplantation of Cornea, 1960, Kiev.

A. P. Nesterov O N. B. Libenson, Sclera, Consolidation of Broad Hip Fascia, 1967.

V. P. Filatov, Curative Use of Preserved Tissues, 1945-Moscow.

*Primary Examiner*—Ronald L. Frinks
*Attorney, Agent, or Firm*—Murray Schaffer

[57] ABSTRACT

The homotransplant for lamellar or layer-by-layer keratoplasty is tendon tissue in the form of sections 50 to 300 microns thick.

The employment of sections of tendon tissue as a homotransplant enables to store at any time any required amount of the plasty material, to preserve this material easily and for long periods. Furthermore, the use of the proposed transplant cuts down the operating time and enhances the clinical outcome of layer-by-layer keratoplasty.

5 Claims, No Drawings

HOMOTRANSPLANT FOR LAYER-BY-LAYER KERATOPLASTY

FIELD OF THE INVENTION

The present invention relates to medicine, and more particularly it relates to ophthalmology, more precisely, to homotransplants used in keratoplasty.

The invention is employed in ophthalmosurgical practice for layer-by-layer or lamellar keratoplasty as a treatment of various kinds of keratitis, ulcers, abscesses, dystrophy of the cornea, keratoleukoma, nebula, vascularized cases included, pseudopterygium, burns, trophic disturbances, trauma, tumors and dermoid cyst of the cornea - in short, in practically every case when layer-by-layer keratoplasty is indicated.

BACKGROUND OF THE INVENTION

There are widely known homotransplants for layer-by-layer keratoplasty in the form of fresh and preserved cornea (cf "Optical Transplantation of Cornea and Tissue Therapy" by V. P. Filatov, in Russian, Moscow, 1945; "Transplantation of Cornea at Complicated Leukoma" by N. A. Puchkovskaya, in Russian, Kiev, 1960).

However, broad introduction of this surgical operation into clinical practice is significantly complicated by difficulties concerned with uninterrupted supply of cadaver eyes to clinics. The ethical considerations of borrowing the eyes from cadavers more often than not are in the way of obtaining the material and providing the stock of preserved cornea. Such difficulties are all but unsurpassable in numerous countries of Asia, America and Africa, stemming as they are from strong national and religious traditions (cf. "Keratoplasty" by R. Paton, New York, 1955).

Moreover, the transplanted cornea in numerous cases displays the tendency to opacify, which means the failure of the conducted operation (cf. the abovecited "Transplantation of Cornea at Complicated Leukoma" by N. A. Puchkovskaya). When keratoplasty is resorted to as the treatment of vascular leukoma and hyperplastic processes of the conjunctiva, cornea homotransplants more often than not become vascularized, which brings about their opacification, and also a recurrence of the disease.

There are also known thinnest transparent films prepared from either fermentation-depolymerized or dispersion-purified skin collagen, or else from cattle tendon, which have been used as heterotransplants for layer-by-layer keratoplasty exclusively in experimental studies and failed to be accepted in the clinical practice (cf. "Collagen-Derived Membrane: Corneal Implantation" by M. N. Dunn et al., Am. Journal of Ophthalmology, 1967, Vol. 157, No. 15, pp. 1329–1330; "Lamellar Keratoplasty: Use of a Collagen Graft for Corneal Replacement" by J. Tanner et al., Eye, Ear, Nose Therapy Monthly, 1968, Vol. 7, No. 8, pp. 368–372). The process of preparing such films is both complicated and costly, and can be conducted exclusively under industrial conditions.

There is also known from literature (cf. J. Malbran in Archives of Soc. Ophthal. Hisp. Am., 1954, Vol. 14, p. 1167) the use of tendons as the homoplasty material for some ophthalmological operations (with the sclera and lids). However, there have been no data available on the use of tendons for plasty of such highly differentiated tissue of the eye as the cornea.

Thus, the hitherto known transplants used for layer-by-layer or lamellar keratoplasty fail to satisfy the demands of the countries that need them. This can be vividly perceived from an analysis of ophthalmological diseases in different nations. Thus, according to the data available from the World Health Organization (WHO) - cf. Chronicle of WHO, 1979, Vol. 1, No. 1 - there are 40 million people in the world suffering from trachoma, and in 6 million cases this disease had resulted in blindness. The highly developed nations of Europe and America likewise have a considerable demand for the plasty material, their blindness index being within the range from 0.2 to 0.7%. In the USA alone (blindness index 0.2%) blindness was caused in 4.7% of the cases by various lesions of the cornea and conjunctiva. In real figures, this percentage means dozens of thousands of humans requiring layer-by-layer keratoplasty.

BRIEF DESCRIPTION OF THE INVENTION

It is an object of the present invention to provide a readily available plasty material for layer-by-layer keratoplasty that would enable to stock it in sufficient quantities.

This and other objects of the invention are attained in that there is proposed a homotransplant for layer-by-layer or lamellar keratoplasty, which, in accordance with the invention, is essentially tendon tissue in the form of sections 50 to 300 microns thick.

DETAILED DESCRIPTION OF THE INVENTION

The tendon tissue to be used as the homotransplant for layer-by-layer keratoplasty is taken in a morgue from human dead bodies under unsterile conditions. Pieces of the tendons, e.g. tendo m. palmaris longus, tendo m. extensor digitorum, tendo m. biceps brachii of a size of about 1.0 by 1.0 by 0.5 cm are deep-frozen with aid of ethyl chloride. Subsequently, sections 50 to 300 micron thick are prepared from these pieces by any suitable known technique with the use of a microtome.

Sections substantially thinner than 50 microns become insufficiently strong when fixed with sutures.

Sections thicker than 300 microns are practically useless on account of their poor acceptance.

Preservation and sterilization of the sections of the tendon tissue can be effected in any suitable known per se manner. However, 70-percent solution of ethyl alcohol seems to be the most simple yet effective approach.

Homotransplants can be packaged both in glass bottles and polyethylene film.

The storage period of the plasty material thus obtained at ambient temperature from 0° C. to +30° C. is unlimited, and the ease of its handling and transportation is obvious.

We have already used homotransplants stored from periods from 7 days to 4 years.

Clinical implementation of the proposed homotransplant had been preceded by experimental observations.

Two series of experiments had been staged with 68 test animals (rabbits). One of the two series had been grafted with the homotransplant of the tendon tissue kind, and the other series - with cornea homotransplants.

The outcome of the operations was studied by the biomicroscopic and morphologic methods on the 7th, 14th, 21st, 30th, 60th, 90th and 180th day.

The experimental studies had shown that the homotransplant of the tendon tissue was well shaping by the shape of the defect and well retained by the sutures, with rapid epithelization of the transplant and its gradual replacement by the cornea's own tissue yielding stable clinical and cosmetic effect of the operation.

Clinically, this was displayed by gradual, in two to four months, clarification of the implanted tendon tissue.

Replacement of the tendon tissue by the transparent cornea tissue was observed in 94.2 percent of the cases, while in the check series the transparent acceptance of cornea amounted to 81.4 percent.

A characteristic feature of the post-surgery period in the cases of layer-by-layer keratoplasty with the proposed homotransplant was a reactive acceptance of the implanted tissue, with no immunologic crises.

The positive outcome of the experimental studies has enabled to launch the development of the techniques of the operation and its broad implementation. The techniques of the operation with the use of the new homotransplant amount to the following. Prior to the operation, one section of the tendon tissue 50 to 300 microns thick is put into a physiologic salt solution with antibiotics added. Following layer-by-layer cutting away of the pathologic focus of the cornea (e.g. leukoma or infiltrate) down to transparent layers, the transplant is shaped to the defect shape and fixed by sutures at the edges.

In three to five days the transplant becomes epithelized. Its clarification begins on the 15th to 25th day. Following 2 to 5 months, completely transparent cornea appears in the transplant's place.

Up to the present time, remote results of the operations (up to 7 years) have been observed, and 262 clinical cases have been operated upon (296 eyes).

In cases where transparent layers of the cornea were reached during the operation, the replacement of the transplant by the transparent tissue was observed in 88.9 percent of the cases. The best results were obtained in cases of cornea distrophy and pterygium.

Layer-by-layer keratoplasty with a homotransplant in the form of tendon tissue produces a well-expressed curative effect, whereby it is applicable as keratoplasty for treatment of purulent ulcera, keratitis, recent burns. By the data in our possession we can state that the curative effect of keratoplasty with the tendon tissue is significantly more pronounced than that associated with lamelar implanation of cornea. In cases of layer-by-layer keratoplasty as treatment of vascularized leukoma (as an aftereffect of burns), the use of the homotransplant in the form of tendon tissue yields somewhat higher clinical results, as compared with the use of cornea homotransplants. Combined auto- or homoplasty of the conjunctiva does not affect the outcome of keratoplasty with the homotransplant in the form of tendon tissue.

The proposed homotransplant in the form of the tendon tissue offers a series of advantages.

The fact that from one human dead body there can be obtained the amount of plasty material sufficent for hundreds of operations means that sufficient quantities of the material can be always available.

The borrowing of tendons offends no national or religious tradition of most various peoples.

The possibility of simple preservation and prolonged storage of sections of the tendon tissue enables to transport the material easily. For the same reason there may be set up centralized facilities for obtaining and preserving the plasty material, with its subsequent distribution among clinics.

A permanent stock of the plasty material enables to operate any fresh case without delay, since there is no waiting for the material that will eventually come from the morgue, whereby the residence of a patient in the hospital or clinic is shortened. The operation time itself is shortened, since not time is spent on stratifying the donor cornea.

Smooth, areactive acceptance of the tendon tissue homotransplant significantly curtails the post-operation convalescence period.

Costly immunity-depressing medicines are used in smaller quantities.

Layer-by-layer or lamellar keratoplasty with employment of the proposed homotransplant is highly clinically effective and is not inferior to lamellar or layer-by-layer transplantation of cornea.

With the tendon tissue being replaced by the cornea's own tissue, the operation produces a stable and prolonged effect. With keratoplasty in cases of hyperplastic processes of the conjunctiva (pterygium or false pterygium as an aftereffect of burns), relapses of the desease are prevented to a significant degree, owing to the proposed homotransplant opposing the growth of blood vessels into the cornea.

For the same reason, the use of the proposed homotransplant enhances the outcome of layer-by-layer keratoplasty in cases of vascularized leukoma, which in general are difficult and adverse cases for implantation of the cornea.

What we claim is:

1. A homotransplant for layer-by-layer keratoplasty, which is essentially human tendon tissue in the form of sections 50 to 300 microns thick.

2. The homotransplant of claim 1, wherein said tissue is stored, prior to use, and after sterilization at a temperature of 0° to 30° C.

3. The homotransplant of claim 2, wherein said sterilization is effected by 70% ethyl alcohol.

4. The homotransplant of claim 1, wherein said tissue is prepared for use, after storage, by placement in a physiologic salt solution with antibiotics added.

5. The method of preparing a homotransplant for use in layer-by-layer keratoplasty which comprises:
   (a) removing tendon tissue from human cadavers;
   (b) deep-freezing said tissue;
   (c) preparing sections 50 to 300 microns thick from said frozen tissue with the use of a microtone;
   (d) preserving and sterilizing said sections;
   (e) packaging the product of step (d) and storing same at 0° to 30° C.; and
   (f) at the time of use, transferring said sections into a physiological salt solution with antibiotics added.

* * * * *